United States Patent [19]

Rusnak

[11] Patent Number: 5,083,862
[45] Date of Patent: Jan. 28, 1992

[54] LIQUID BUBBLE DETECTOR

[75] Inventor: Miro Rusnak, LaVerne, Calif.

[73] Assignee: City of Hope, Duarte, Calif.

[21] Appl. No.: 565,984

[22] Filed: Aug. 13, 1990

[51] Int. Cl.⁵ .................. G01N 21/89; G01N 21/05
[52] U.S. Cl. .................. 356/237; 250/574; 356/440
[58] Field of Search .............. 250/574, 573; 356/246, 356/440, 410

[56] References Cited

U.S. PATENT DOCUMENTS

| | | | |
|---|---|---|---|
| 3,812,482 | 5/1974 | Clark | 250/573 X |
| 4,344,429 | 8/1982 | Gupton et al. | 250/574 X |
| 4,529,306 | 7/1985 | Kilham et al. | 250/574 X |

Primary Examiner—Vincent P. McGraw
Attorney, Agent, or Firm—Edward S. Irons

[57] ABSTRACT

A device for detecting the flow of fluid through the lumen of a transparent or translucent tube and the presence or absence of bubbles in such flowing fluid is disclosed.

3 Claims, 1 Drawing Sheet

LIQUID BUBBLE DETECTOR

This invention relates to a detector useful to determine whether liquid is passing through a tubular liquid conduct aid, and if so, whether said liquid includes bubbles.

BACKGROUND OF THE INVENTION

Many automated chemical analysis instruments include tubular transfer means or the like for conducting samples into other instrument elements. Various bubble sensors are known in which a photodetector such as a photodiode or phototransistor diametrically opposed (180°) to a light source such as a light emitting diode (LED) to detect air bubbles in fluid flowing through the lumen of a tube. Bubbles are detected by such devices as a consequence of the reduction in optical coupling caused by the presence of bubbles in fluid flowing through the tube lumen.

There appears, however, to be a paucity of prior art teaching of devices useful to detect the presence or absence of fluids flowing through tube lumens and also the presence of bubbles in such flowing fluids.

SUMMARY OF THE INVENTION

This invention provides a device useful to determine whether or not a fluid is flowing through the lumen of a fluid transferring translucent tube, and if so, whether such fluid of flowing contains bubbles. The invention has a particularly significant application to high performance liquid chromatography (HPLC).

DETAILED DESCRIPTION OF THE INVENTION

This invention provides a simple, inexpensive device for determining whether or not a fluid passing through a translucent fluid transfer tube and if so whether said flowing fluid contains bubbles.

Figure 1:
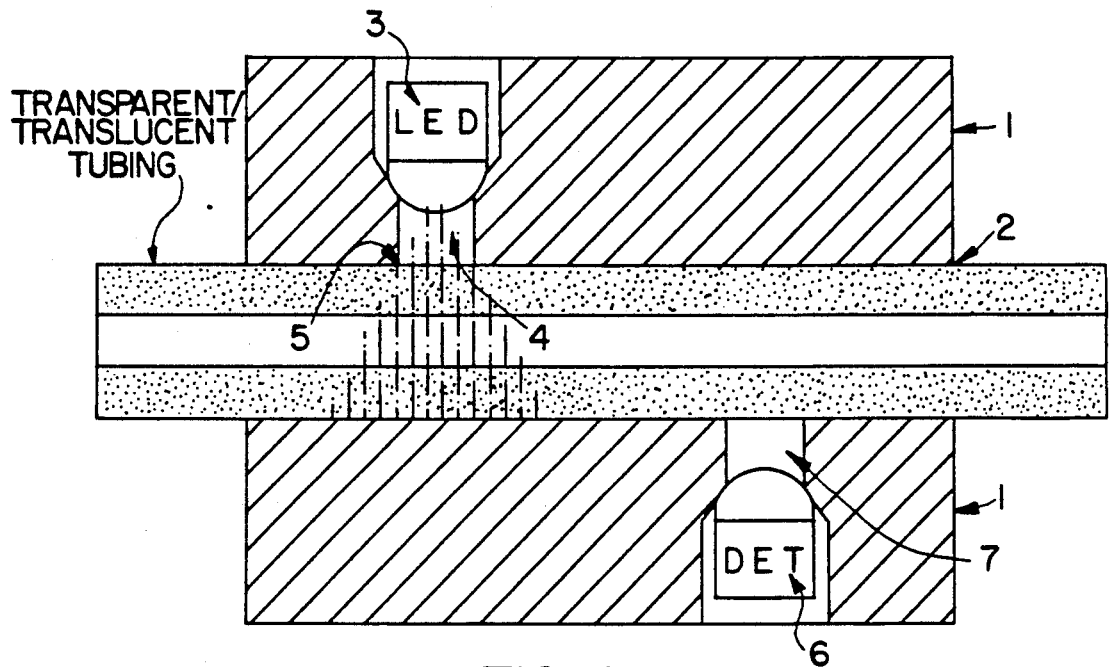
FIG. 1 depicts the device of the invention under conditions such that no fluid is flowing through the lumens of a translucent fluid transfer tube.
Figure 2:
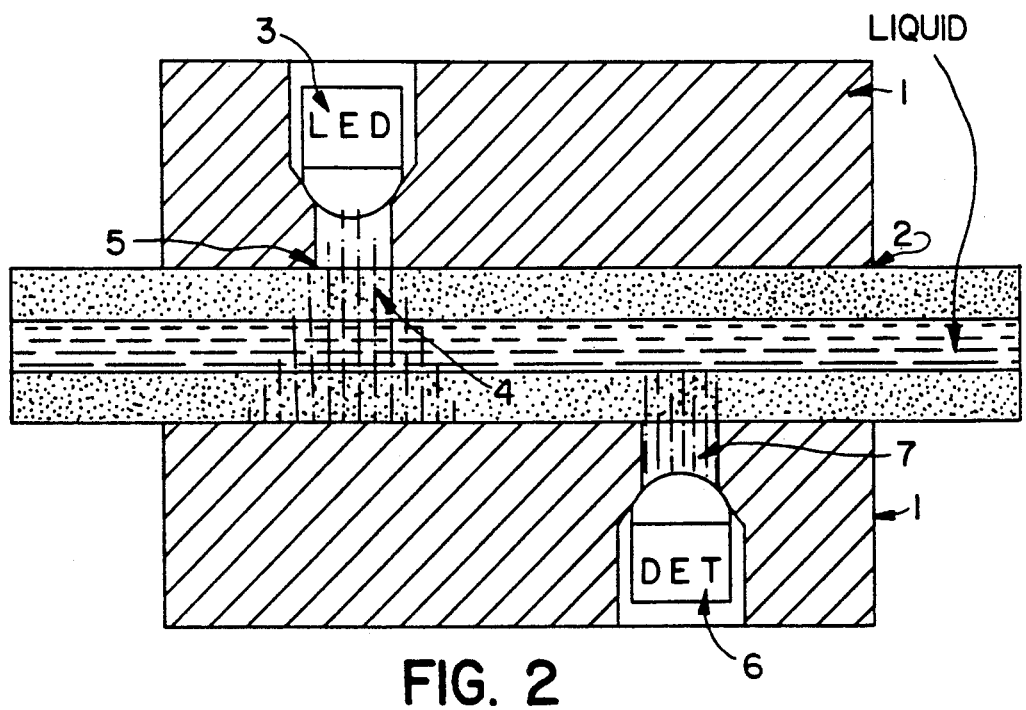
FIG. 2 depicts the operation of the device of the invention with fluid flowing through the lumen of a translucent fluid transfer tube.

Referring to FIG. 1 the device of the invention is shown in association with a translucent fluid transfer tube through which no fluid is flowing. The device includes a housing for a transparent or translucent fluid transfer tubing 2. The housing includes a light emitting diode (LED) 3 with access means 4 to the wall 5 of the tubing 2.

The housing also includes a detector 6 with access 7 opposed, e.g., (180°) to the portion of the tubing 2 to which the LED 3 has access to the tubing 2.

The detector 6 and its access 7 is positioned downstream from the LED 3 and its access means 4 to the wall of the tube 2.

In operation, in the preferred embodiment of the invention, the LED 3 emits infrared indication through the wall of the tubing 2. The detector 6 is offset downstream so that light from the LED is not detected when the tube 2 is empty.

When liquid is present in the tube 2, it acts as a light transmitter, thus permitting the detector 6 to detect light from the LED 3.

The consequent signal may be processed by a simple and conventional electronic circuit with total transistor logic (TTL) output.

A practical application of the invention entails positioning the housing 1 at the outlet of an HPLC injector to indicate when the injector is "full." A "full" signal is sent to a computer which terminates sample delivery. Thus, very little of the sample is wasted. About 95% by weight of the sample is injected into the HPLC when the device of the invention is used. In systems which do not use the device of the invention, only about 50% of the sample is injected into the HPLC.

The device of this invention has been tested in association with an HPLC instrument with teflon tubing with an outer diameter (OD) of 1/16 inches and an internal diameter of 0.8; 0.5 and 0.2 mm (30, 20, and 10 thousandths of an inch) and with similar teflon tubing of ⅛ inch OD.

I claim:

1. In a device for detecting the flow of fluid through the lumen of a transparent or translucent tube and the presence or absence of bubbles in said fluid, said device including light emitting means for emitting light into said lumen and detector means for detecting the presence of said emitted light in said lumen, the improvement of which comprises said detector means being out of optical alignment with and located downstream from said light emitting means.

2. A device, as defined by claim 1, in which said light emitting means is a light emitting diode.

3. A device for detecting the presence or absence of a fluid flowing through the lumen of a transparent or translucent tube which comprises a housing for a transparent or translucent fluid transfer tube;

light emitting means positioned in said housing to emit light into the lumen of said tube;

light detector means positioned in said housing to detect the presence or absence of light emitted by said light emitting means into a fluid flowing through said lumen of said tube;

said light detector means being optically misaligned with said light emitting means to preclude light detection when no fluid is present in said lumen of said tube.

said light detector means being optically misaligned with said light emitting means to preclude light detection when no fluid is present in said lumen of said tube.

* * * * *